US 6,628,744 B1

(12) United States Patent
Luhta et al.

(10) Patent No.: US 6,628,744 B1
(45) Date of Patent: Sep. 30, 2003

(54) OFF-FOCAL RADIATION CORRECTION IN CT

(75) Inventors: Randall P. Luhta, Highland Heights, OH (US); Kevin M. Brown, Mentor on the Lake, OH (US); Steven J. Utrup, Willoughby, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1 day.

(21) Appl. No.: 10/256,059

(22) Filed: Sep. 26, 2002

(51) Int. Cl.$^7$ ................................................ A61B 6/03
(52) U.S. Cl. ........................................ 378/15; 378/901
(58) Field of Search ........................... 378/4, 8, 15, 19, 378/901

(56) References Cited

U.S. PATENT DOCUMENTS 4,809,172 A  *  2/1989  Hopkinson et al. ............ 378/4

5,757,951 A  *  5/1998  Tuy ............................ 382/131

* cited by examiner

Primary Examiner—David V. Bruce
(74) Attorney, Agent, or Firm—Fay, Sharpe, Fagan, Minnich & McKee LLP

(57) ABSTRACT

A third generation CT scanner includes a rotating x-ray source (18) and a detector array (16). Each sampling of the detector array generates a source fan data line of data values that are converted (34) to attenuation values in a logarithmic domain and subject to preliminary corrections (36). Attenuation values from a plurality of adjoining source fans are converted (94) back to a non-logarithmic domain as intensity values. A corresponding deconvolution function (88) from a deconvolution function look-up table (90) corresponding to the detector whose intensity value is being corrected is deconvolved with a line (84) of the intensity values which spans a plurality of adjoining source fan data lines to remove the intensity attributable to off-focal radiation (30). The intensity data is converted (102) back into attenuation values in the logarithmic domain and reconstructed (106) into an image representation for display on a monitor (112).

21 Claims, 11 Drawing Sheets

OFF-FOCAL RADIATION CORRECTION IN CT

BACKGROUND OF THE INVENTION

The present invention relates to the diagnostic imaging arts. It finds particular application in conjunction with third generation CT scanners and will be described with particular reference thereto.

A third generation CT scanner includes a rotating gantry, which rotates about a central axis of a patient-receiving bore. The rotating gantry carries an arc of x-ray detectors on one side and an x-ray tube diametrically across the patient-receiving bore from the arc of detectors. The x-ray tube includes a collimator disposed outside of the vacuum envelope, which limits the x-ray beam to a fan-shaped swath that spans the arc of detectors. Typically, the collimator opening is about 4–5 cm in the circumferential direction and the thickness of the slice(s) in the axial direction is about 1–10 mm.

As the gantry rotates, the detectors are repeatedly sampled, typically 1000–2000 times per revolution. The intensity of radiation received by each detector is assumed to be the intensity of radiation that has traversed the straight-line path from the focal spot of the x-ray tube to the detector. While the majority of the radiation originates at the focal spot and substantially follows this line, a significant amount of radiation, known as off-focal radiation, originates at other points in the x-ray tube.

In a rotating anode x-ray tube, an anode, which is typically 15–20 centimeters in diameter, is rotated at a high rate of speed. A beam of electrons is focused to form a focal spot on the order of a millimeter in diameter on the rotating anode. While the majority of electrons strike the anode at the focal spot, a significant number of electrons are scattered and strike other portions of the rotating anode. This creates an x-ray source that has a bright center point at the focal spot and a haze of off-focal radiation around it. This off-focal radiation tends to blur the edges of imaged objects, and is especially noticeable at the interface between bone and soft tissue. This blurring often manifests itself in a halo artifact in the reconstructed image.

Previously, the edge artifact was reduced by using edge-enhancing filters. While edge-enhancing filters do help sharpen the edges, they do not make an actual correction for the off-focal radiation.

The present invention provides a new and improved off-focal radiation correction.

SUMMARY OF THE INVENTION

In accordance with one aspect of the present invention, a method of generating a diagnostic image is provided. An x-ray source and a detector array are rotated concurrently around a subject in an examination region. An intensity of x-rays which have traversed the subject are measured with the array of radiation detectors. Each detector generates an electronic data value which includes an on-focal radiation component and an off-focal radiation component. The array of detectors are sampled concurrently as the source and detector array rotate to generate a series of source-fan data lines. The source-fan data lines are corrected for off-focal radiation. The off-focal radiation corrected lines are reconstructed into an image representation.

In accordance with another aspect of the present invention, an apparatus is provided for generating diagnostic images. A rotating gantry is mounted for rotation about a subject-receiving bore. An x-ray source is mounted to the rotating gantry. An array of x-ray detectors are mounted to the rotating gantry across the subject-receiving bore from the x-ray source. The detectors measure an intensity of x-rays which have traversed the subject. Each detector generates an electronic data value which includes an on-focal radiation component and an off-focal radiation component. A sampling means samples the array of detectors concurrently as the x-ray source and detector array rotate to generate a series of source-fan data lines. A correcting means corrects the source fan data lines for off-focal radiation. A reconstructing means reconstructs the off-focal radiation corrected data lines into an image representation.

One advantage of the present invention resides in higher quality images.

Another advantage of the present invention resides in a reduction of off-focal radiation artifacts.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
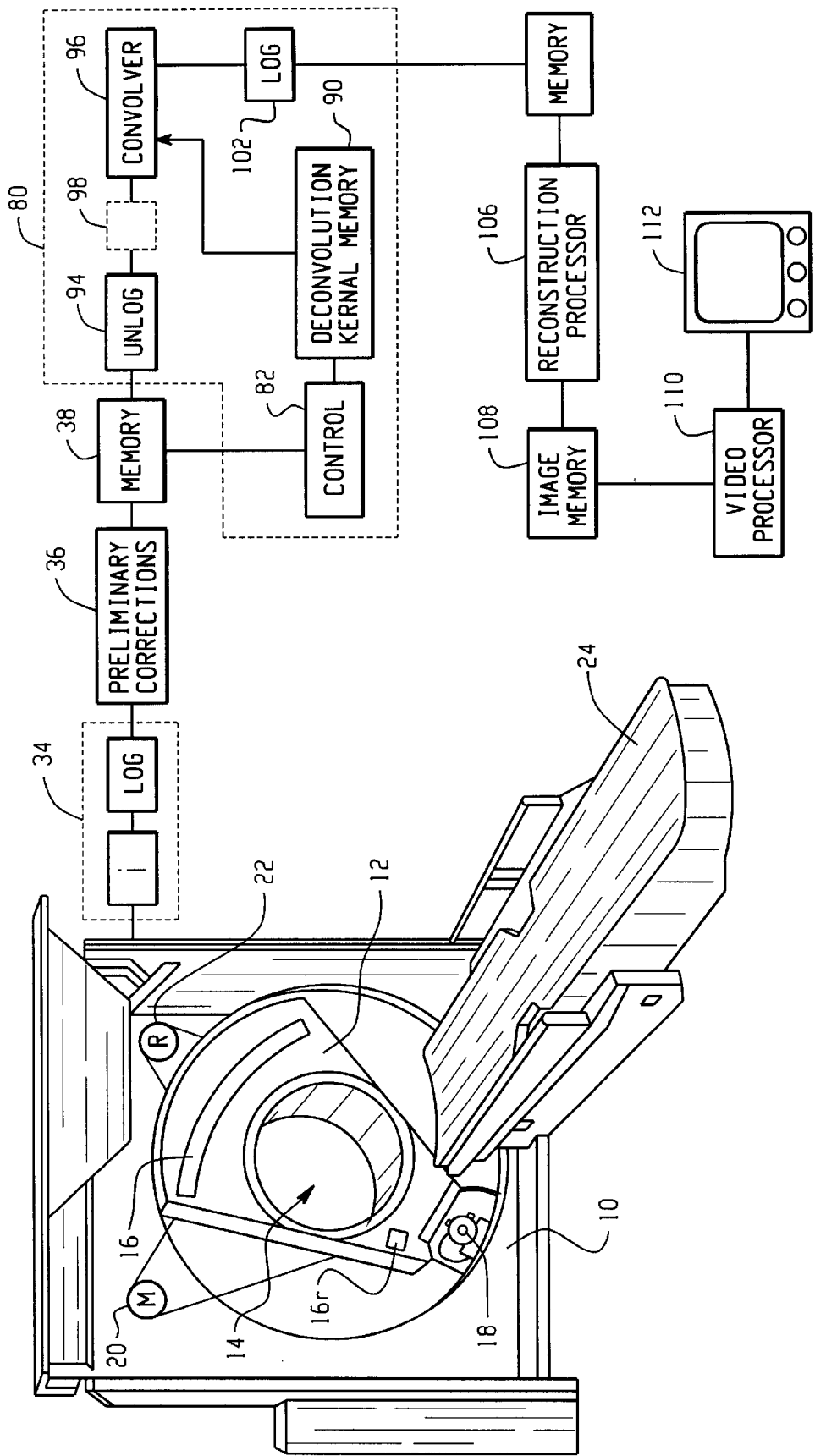
FIG. 1 is a diagrammatic illustration of a CT scanner in accordance with the present invention.

With reference to FIG. 1, a CT scanner includes a stationary gantry 10 within which a rotating gantry 12 is mounted for rotation about a subject-receiving bore 14. The rotating gantry carries an arc of radiation detectors 16 and an x-ray tube 18 which is disposed across the subject receiving bore 14 180° opposite a center of the detector arc. An appropriate motor or drive 20 rotates the rotating gantry at a speed of preferably 60–120 RPM. An angular position resolver 22 determines the instantaneous angular position of the rotating gantry. A subject support or couch 24 supports a subject in the subject-receiving bore 14. For volume imaging, the subject support also indexes the subject axially through the bore.

A reference detector $16_r$ detects the instantaneous intensity of radiation from the x-ray tube that has not been attenuated by the subject. Each detector in the detector arc 16 outputs a signal that is indicative of the currently received radiation intensity, i.e., the intensity of radiation after it has been attenuated along a path through the subject.

As the rotating gantry 12 rotates, the detectors 16 are repeatedly sampled, preferably about 1100–1200 times per revolution. The position of the focal spot on the anode of the x-ray tube is preferably electronically toggled and sampling again in each toggled position to double the number of samplings per revolution. In this manner, a set of fan beam data is sampled at about 0.16° angular increments.

Figure 2:
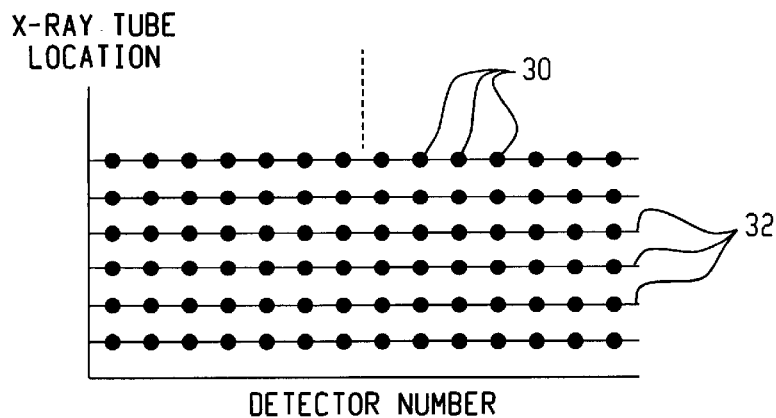
FIG. 2 illustrates organization of data lines in memory.

With continuing reference to FIG. 1 and further reference to FIG. 2, each time the detectors are sampled, a set of fan beam data or data line of digital values 30 is generated. When the x-ray tube rotates to the next sampling position, another data line 32 of digital values is sampled, and so forth. At the gantry, data compression circuitry 32 subtractively combines each sampled intensity value with the reference intensity value and converts to the log to form an attenuation value. Each attenuation data line is coupled with an identification of the x-ray source position from the angular resolver 22, and an indication of the detector, hence angular position within the fan, for each attenuation value.

A preliminary correction processor 36 makes preliminary corrections on the attenuation values as are known in the art. The corrected data lines 32 are stored in an attenuation data memory 38 as lines 32 of data values 30 are indexed by the source position as illustrated in FIG. 2.

Figure 3:
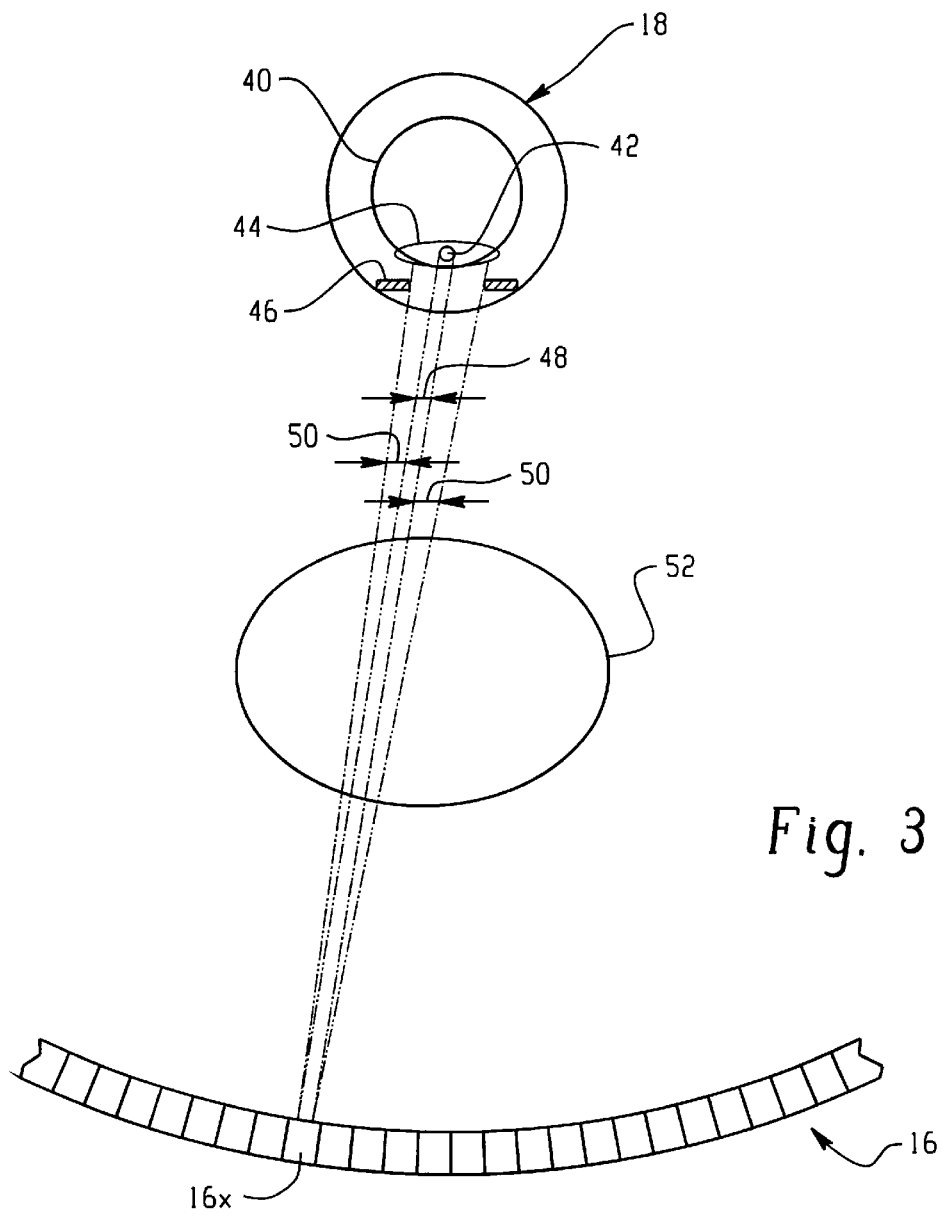
FIG. 3 is a diagrammatic illustration showing the contribution of off-focal radiation.
Figure 4A:
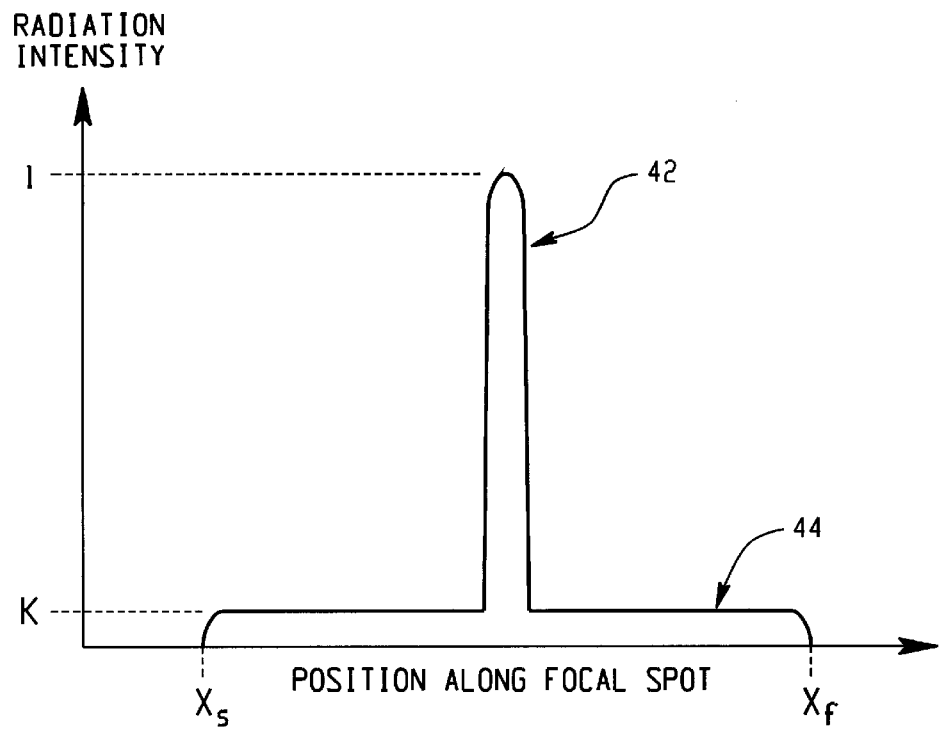
FIG. 4A illustrates a radiation profile of radiation.
Figure 4B:
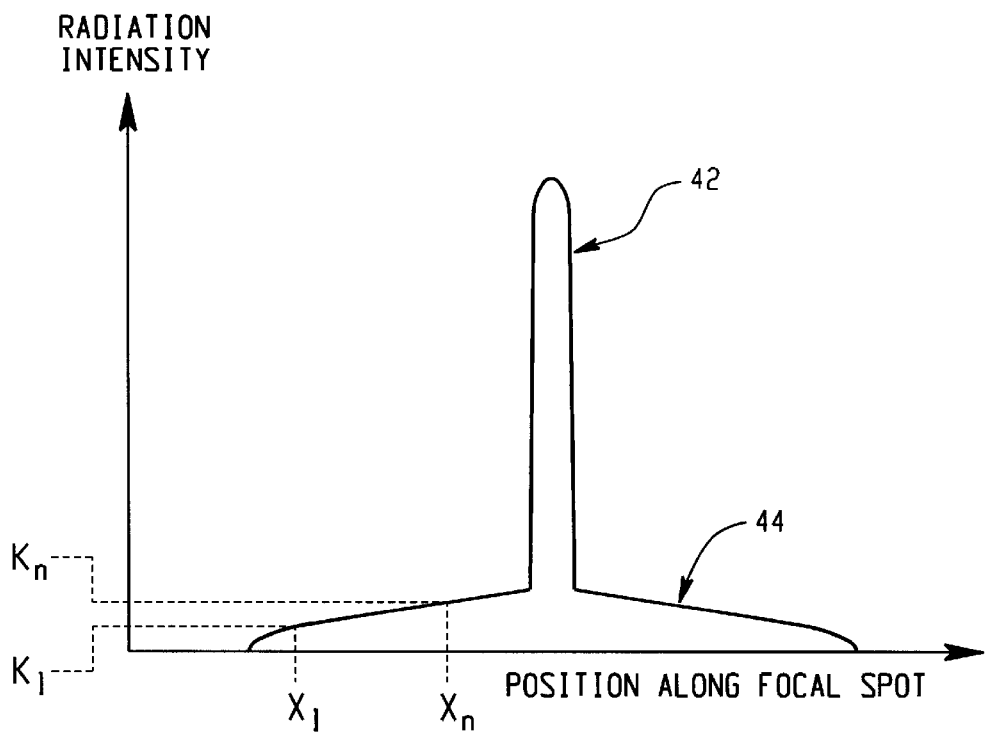
FIG. 4B is another profile of x-ray radiation across the aperture of the x-ray tube.

With reference to FIG. 3, the x-ray tube 18 includes an anode 40 on which an electron beam is focused at a focal spot 42. Scattered electrons strike other portions of the anode and other metal structures in the tube creating a background of off-focal radiation 44. The range of the off-focal radiation visible to the detectors is limited by a collimator 46. Radiation from the focal spot creates a focal ray 48 while the off-focal radiation 44 creates a penumbra of surrounding off-focal rays 50. As illustrated in FIG. 4A, the vast majority of the radiation originates from the focal spot 42 with a significant level of off-focal radiation 44 around the focal spot. In FIG. 4A, the off-focal radiation intensity is modeled as a constant. In FIG. 4B, the off-focal radiation is modeled with a higher intensity adjacent the focal spot and a diminishing intensity outward. The exact radiation model is determined by the x-ray tube selected.

Figure 5:
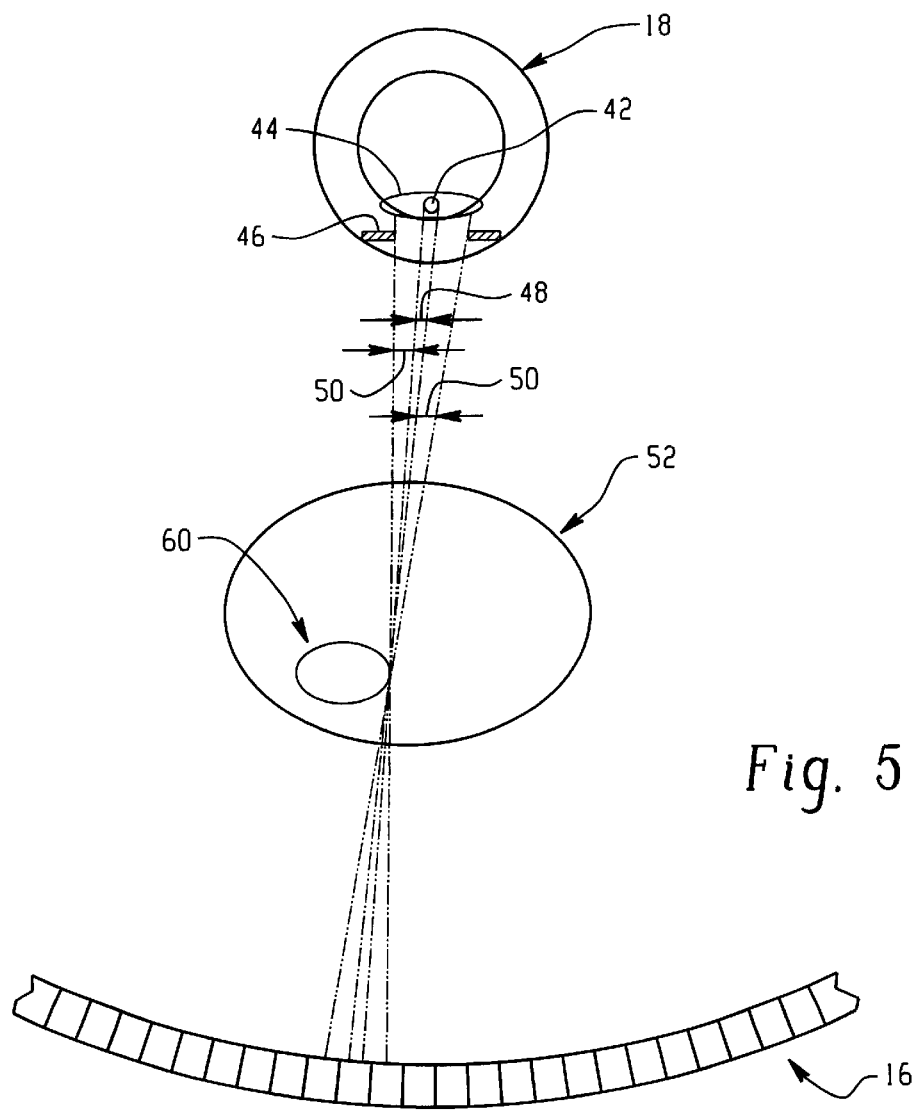
FIG. 5 illustrates the interaction of off-focal radiation with the edge of an object.
Figure 6:
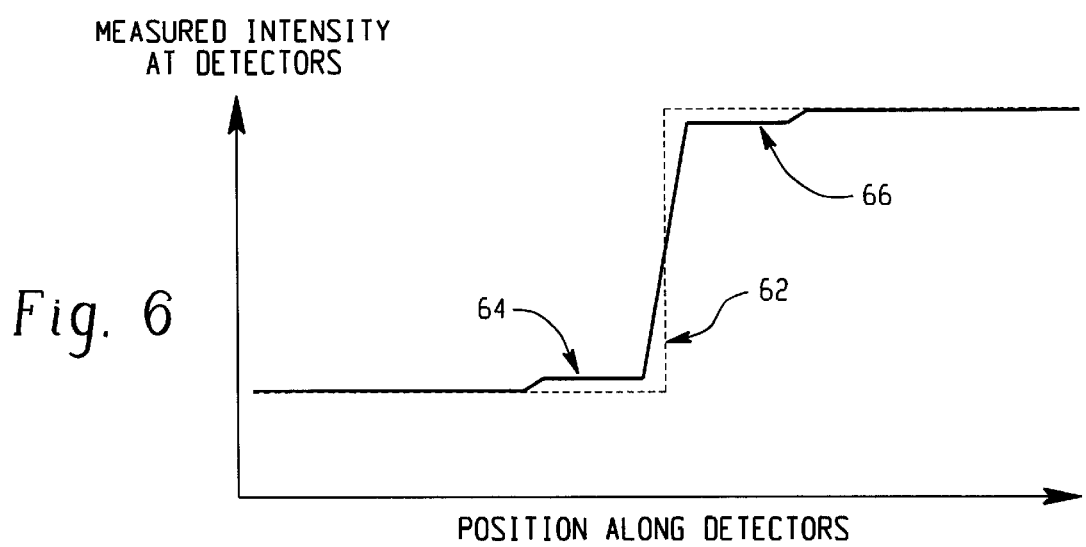
FIG. 6 illustrates the effect of off-focal radiation versus an ideal edge profile.
Figure 7:
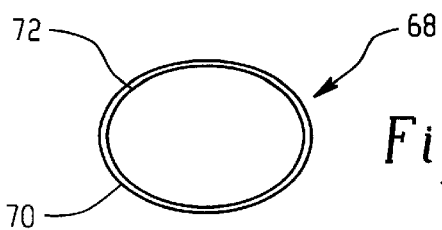
FIG. 7 illustrates the halo effect attributable to the off-focal radiation disturbance of edge profiles.

With reference to FIG. 5, off-focal radiation has its most notable effect at edges of objects in the CT image. An exemplary object 60 in the subject has its edge along the focal ray 48. As the focal ray and the off-focal rays pass the edge of the object, they project onto the detector array 16 with a typical intensity profile, such as shown in FIG. 6. An ideal edge profile 62 is an abrupt transition from one intensity to another. The off-focal radiation causes a pedestal level on each side of the ideal step. On the low intensity side of the step, there is a slight increase in intensity 64 and on the high intensity side, there is slight decrease in intensity 66. The effect of this edge intensity profile at the detector is to cause a halo in a reconstructed image 68 as shown in FIG. 7. For an object that is denser than its surroundings, the pedestal on the low energy side 64 of the transition causes an inner halo 70 and the pedestal on the high energy side 66 causes an outer halo 72.

Figure 8:
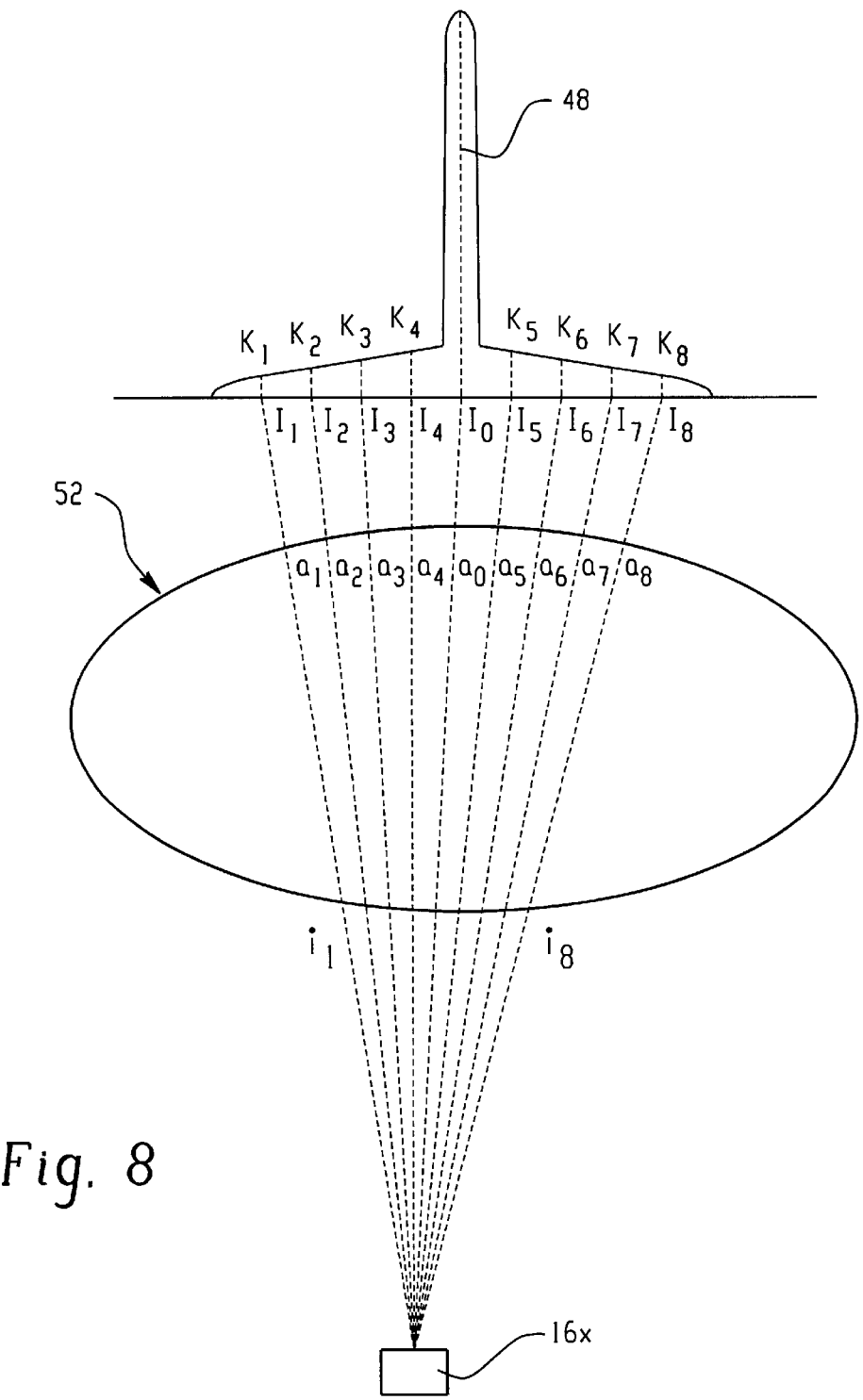
FIG. 8 illustrates the focal and off-focal radiation contribution to an exemplary detector.

With reference to FIG. 8, the focal ray 48 has an initial intensity $I_0$. Radiation along rays initiating at positions $K_1-K_n$ has corresponding intensities $I_1-I_n$ as depicted by the radiation profile of FIG. 4B. These nine rays are attenuated with attenuation values $a_0-a_8$ as they pass through a subject 52, resulting in intensities $i_0-i_8$ emerging from the subject. These intensities are summed by an exemplary detector $16_x$. Of course, the CT scanner attributes all of the intensity to the focal ray 48 and assumes that the sum is $i_0$. The present off-focal radiation correction estimates and subtracts the off-focal intensities $i_1-i_8$ from the sum to provide $i_0$ more accurately.

Figure 9B:
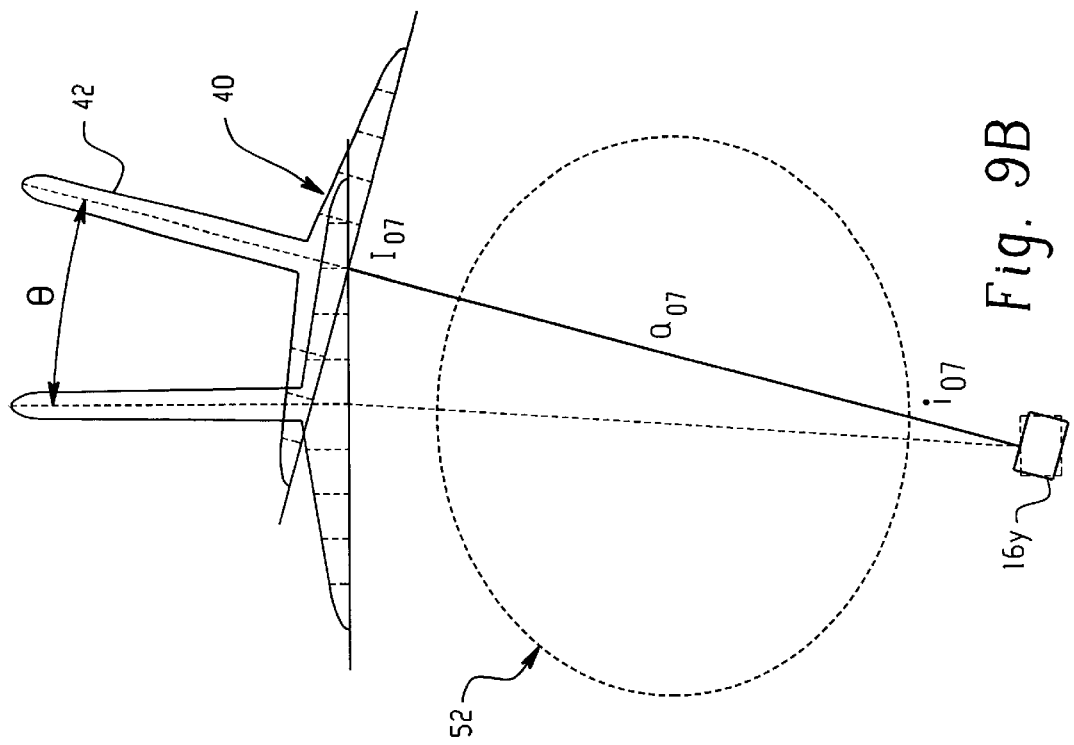
FIGS. 9A and 9B illustrate estimation of off-focal radiation from the focal ray in other detector fans.
Figure 9A:
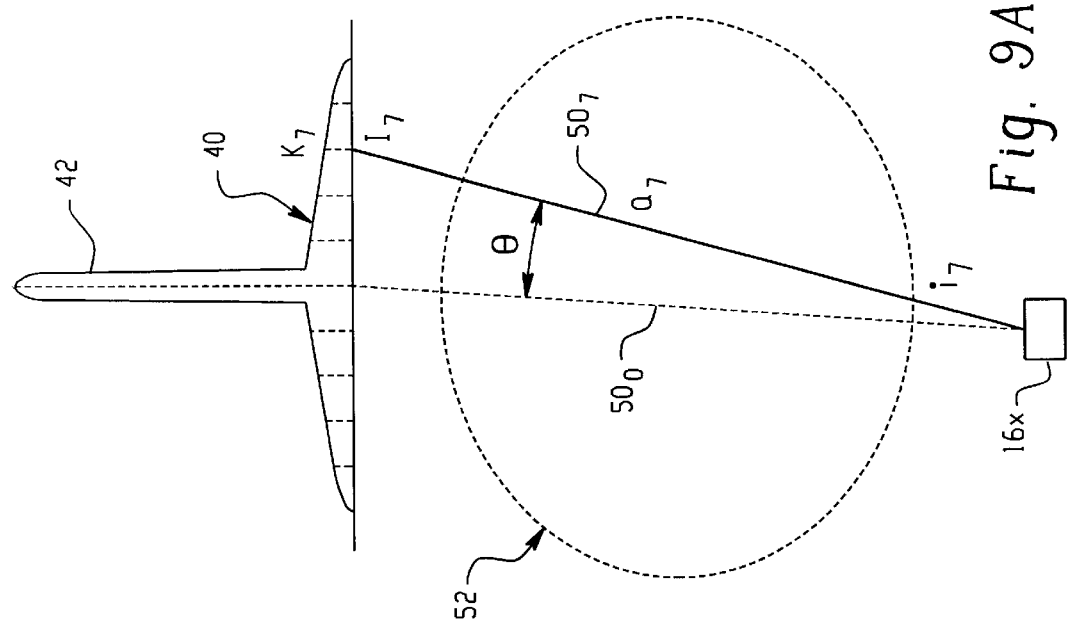

With reference to FIGS. 9A and 9B, it will be seen that each off-focal ray for one sampling of a detector substantially follows the same line as the focal ray sampled by a different detector in a different source position. In the example of FIGS. 9A and 9B, the focal ray extending between the x-ray source 18 in an angularly displaced position $k_7$ by angle $\theta$ and a different detector $16_y$ (which has rotated into the position originally occupied by detector $16_x$) follows the same path as off-focal ray 50$_7$ of FIG. 8. Thus, by looking to a different data point in a different data line and using the appropriate weighting, the contribution of off-focal intensity $i_7$ can be determined. The intensity $i$ reaching the detector $16_x$ is reduced in accordance with the off-focal radiation coefficient $K_7$ of the FIG. 4B model and the intensity $i_7$ obtained by detector $16_y$ at the rotational offset $\theta$.

Figure 10:
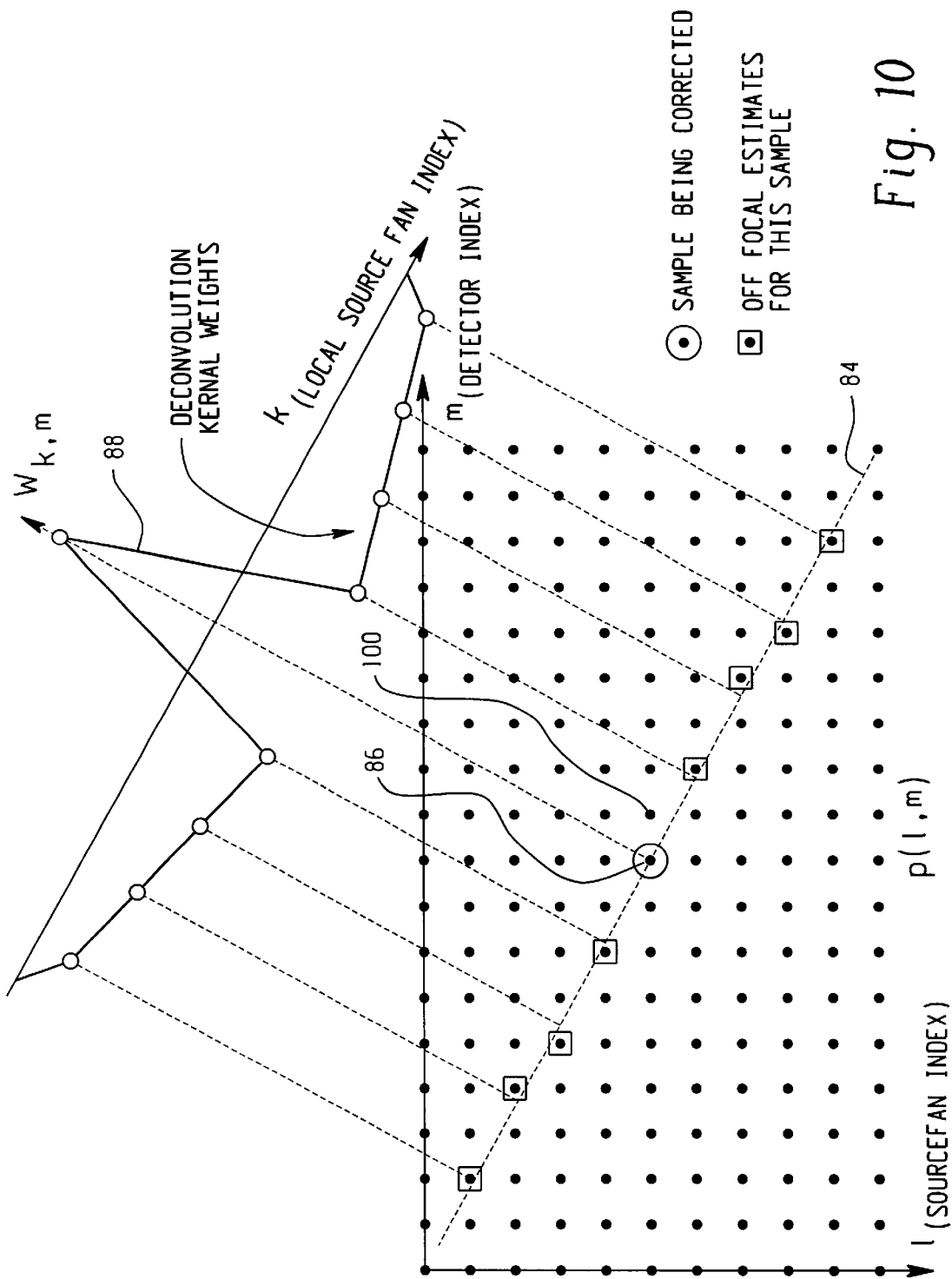
FIG. 10 illustrates correcting of data values in memory using a deconvolution kernel.

With reference again to FIG. 1, an off-focal radiation correction means 80 determines the corresponding ray and intensity correction for each of the off-focal rays $50_1-50_8$ contribution to each of the data values of each intensity line. With reference to FIG. 10, a control circuit 82 determines a line 84 through an exemplary data value 86 in the memory 38 to be corrected. The intensities corresponding to $i_1-i_8$ are defined equi-spaced along the line 84. The controller 82 determines the closest data value from neighboring data lines for each of rays $50_1-50_8$. The control circuit 82 also selects an appropriate deconvolution function 88 that corresponds to the position of exemplary detector 86 within the array 16 from a deconvolution function memory 90. With scatter grids 92, the amount of off-focal radiation reaching each detector changes as does the relative off-focal radiation intensity contribution along each of the off-focal radiation paths.

Once the control circuit 82 selects the corresponding data values from the other data lines in memory 38, an anti-log circuit 94 converts the logarithmic attenuation values $a_0-a_8$ to intensity values $i_0-i_8$ in non-logarithmic notation. A processor 96 multiplies each intensity value $i_0-i_8$ by a corresponding weighting of the selected deconvolution function 88 and combines the values. Because the weighting for the correction intensity values $i_1-i_8$ are all negative, these contributions are all subtracted from the focal ray intensity $i_0$. Although the deconvolution function is exemplified as digitized into nine values, it is to be appreciated that a larger or smaller number of values can be selected. After the data value 86 has been corrected, the line 84 is shifted to a next data value 100 in the data line and the process is repeated.

As each data value is corrected, it is returned to logarithmic notation by a log circuit 102 and stored in a corrected data memory 104. The off-focal radiation corrected data in memory 104 can be further corrected or processed, as is conventional in the art. When a plurality of detector arcs 16 collect a plurality of slices concurrently, the correction process is optionally repeated in the longitudinal direction.

As the data is corrected, a reconstruction processor 106 reconstructs the data lines into an image representation, which is stored in an image memory 108. Convolution and backprojection or other known reconstruction techniques are completed. A video processor 110 selects portions of the image data from the image memory 108, such as a slice, projection, or the like, and converts it into appropriate format for display on a human-readable display 112, such as a video monitor, liquid crystal display, active matrix display, a printer, or the like. Optionally, the data from the image memory is also sent to an archive for storage.

The deconvolution functions stored in memory 90 can be determined by empirical measurements or calculated mathematically. Preferably, the functions are calculated mathematically using the off-focal model:

$$d(s) = X(s) \otimes (\delta(s) + e(s)) \quad (1)$$

where d(s) represents the measured signal, e(s) is the error or off-focal radiation, δ(s) is the on-focal radiation, and X(s) is the target signal. It should be noted that if e(s) goes to zero, then d(s)=X(s) and the measured signal contains no error. Solving for X(s):

$$X(s) \cong 2d(s) - d(s) \otimes (\delta(s) + e(s)) \quad (2)$$

Assuming a δ function of amplitude (1-ofa), Equation 2 becomes:

$$X(s) \cong d(s) + \text{ofa} \cdot d(s) - d(s) \otimes e(s) \quad (3)$$

Defining a deconvolution kernel as w(s)=−e(s)+ofa⋅δ(s) gives:

$$X(s) \cong d(s) + d(s) \otimes w(s) \quad (4)$$

Figure 11:
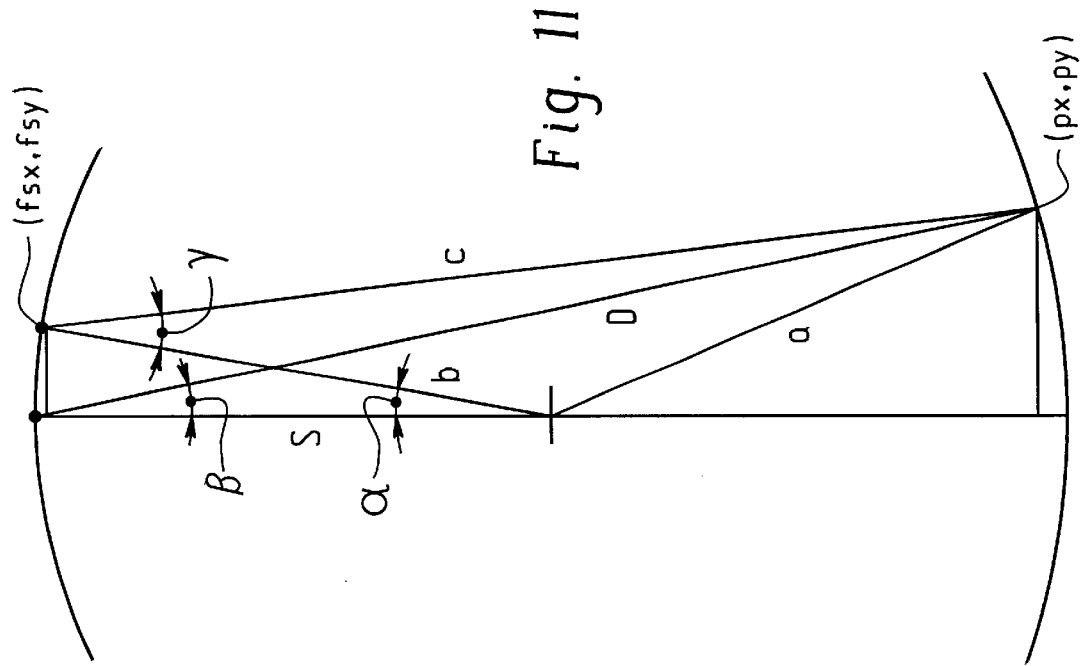
FIG. 11 illustrates a pseudo-detector fan derivation.

With reference to FIG. 11, when a given detector $16_x$ lies at an angle P from the central ray and the off-focal radiation source is an at angle a from the current source position, the first challenge is to identify the detector of the array when the source fan is at the angle a that gives the best off-focal radiation path to the detector that is rotated to the position of detector $16_x$. A detector that lies at an angle β from the central ray has coordinates relative to isocenter given by:

$$px = D \cdot \sin\beta \, py = -(D \cdot \cos\beta - S) \quad (5)$$

where D is a constant source-to-detector distance. Similarly, the x,y position of the second focal spot is given by:

$$fsx = S \cdot \sin\Delta \, fsy = S \cdot \cos\Delta \quad (6)$$

where S is the distance source-to-isocenter (of the bore) distance. Finding the size of the triangle abc of FIG. 11 gives:

$$a = \sqrt{px^2 + py^2}$$

$$b = S \quad (7)$$

$$c = \sqrt{(fsx-px)^2 + (fsy-py)^2}$$

where the formula for c is the distance formula using point (fsx, fsy) and (px, py). The law of cosines gives the angle γ as follows:

$$\gamma = a\cos\left(\frac{a^2 - b^2 - c^2}{-2bc}\right) \quad (8)$$

Because the angle γ can be either positive or negative, the acosine function only gives positive values for small angles, the sign of γ is determined by:

$$ps = py \cdot \tan\alpha \text{ if } ps < px, \text{ then } \gamma = -\gamma \quad (9)$$

The angle γ of the detector is converted into a detector number by:

$$m = \frac{\gamma}{\Delta\beta} + \text{axis\_fs} \quad (10)$$

where Δβ is the angular spacing between detectors and axis_fs is the position of the central ray on the detectors. From these formulas, for each detector in the array, the detectors are computed that are used to estimate the off-focal line integrals that exist over a given range of source angle α. It turns out, that this estimate path is very close to linear over a small angular range and the slope of the line changes only slightly from the left side of the detector array to the right side.

Figure 12:
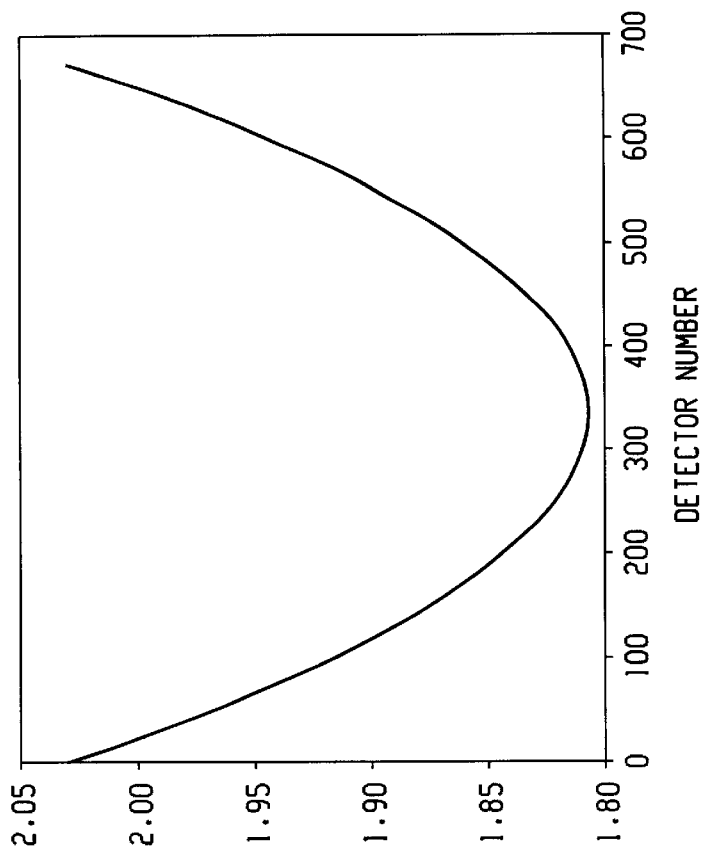
FIG. 12 graphs the mean slope vector.

To compute a detector index from Equation 10 for each detector over a range of source angles a, the means slope vector $S_m$ gives the off-focal estimates for each detector, as shown in FIG. 12. Preferably, $S_m$ is implemented as a precalculated lookup table to speed calculation. Of course, the computation could be made directly from Equation 10, without the expedient of precalculated slope vectors.

Two physical considerations determine the range of (x over which off-focal radiation exists. These considerations include the width an d location of the tube aperture where the x-rays exit the tube and the size and positioning of the anti-scatter grids 92 mounted on the detectors.

Figure 13:
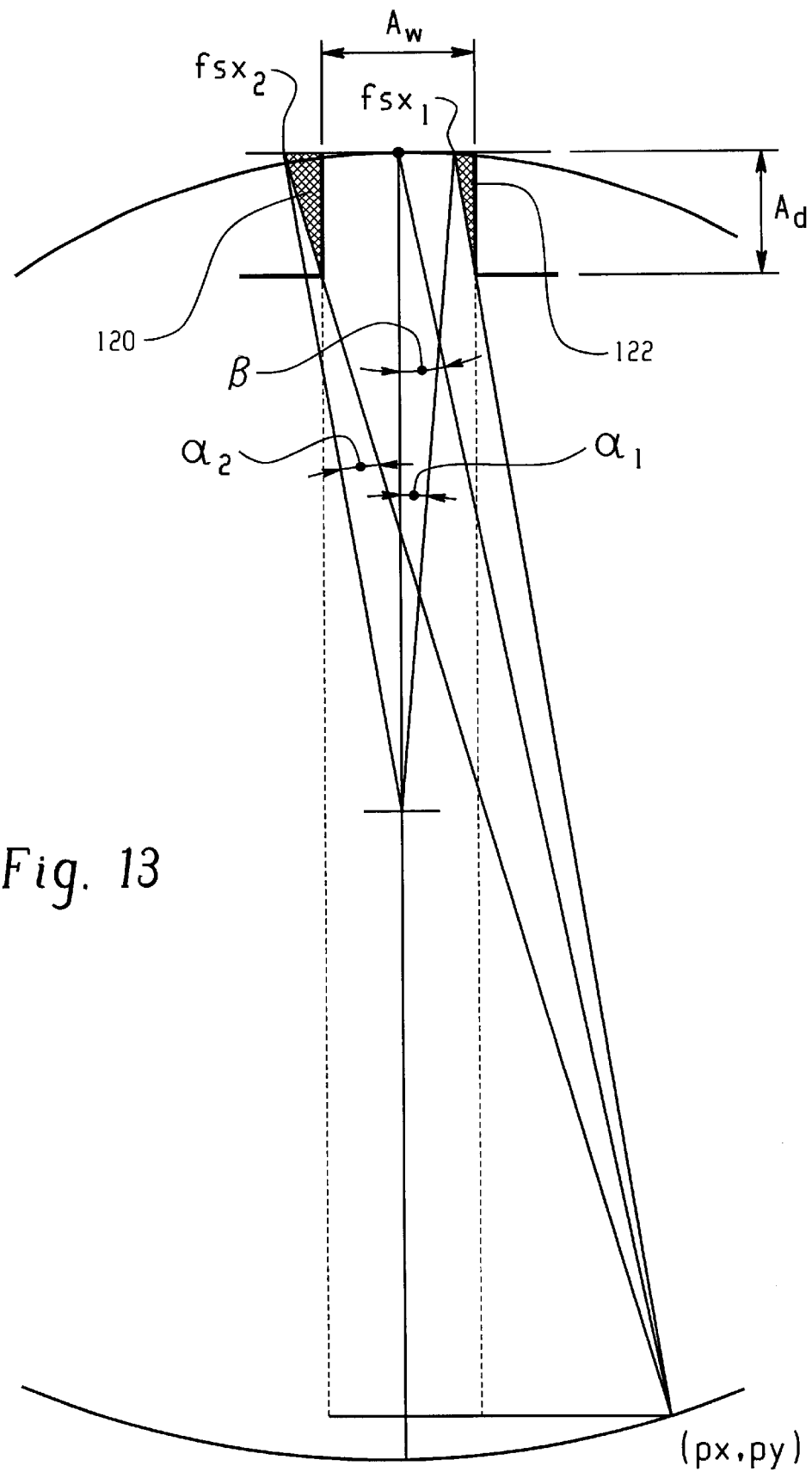
FIG. 13 illustrates an off-focal cut-off due to tube aperture.

With reference to FIG. 13, the position of the detector at angle β is again defined as (px, py). $fsx_1$ and $fsx_2$ are the maximum and minimum points where the detector sees the off-focal radiation. Beyond these points, the off-focal radiation is blocked by the tube aperture. These two points are defined relative to an origin of px and py at the focal spot by:

$$fsx_1 = \frac{A_w}{2} - \frac{A_d \cdot \left(px - \frac{A_w}{2}\right)}{(py - A_d)} \quad (11)$$

$$fsx_2 = \frac{A_w}{2} + \frac{A_d \cdot \left(px + \frac{A_w}{2}\right)}{(py - A_d)} \quad (12)$$

Using similar triangles 120, 122, the source angle that corresponds to each of these points is defined by:

$$\alpha_1 = \tan^{-1}\left(\frac{fsx_1}{S}\right) \quad (13)$$

$$\alpha_2 = \tan^{-1}\left(\frac{fsx_2}{S}\right)$$

These angles represent the maximum and minimum angles where the detector sees the off-focal radiation. Because the correction operates in source-fan increments and the fan is sampled only at regular angular increments $\Delta\alpha$, these angles can be converted into source-fan increments by:

$$sf_1=\text{round}(\alpha_1/\Delta\alpha) \quad sf_2=\text{round}(\alpha_2/\Delta\alpha) \quad (14)$$

These numbers identify the source fans that include the range of data for the removal of all off-focal radiation.

Figure 14:
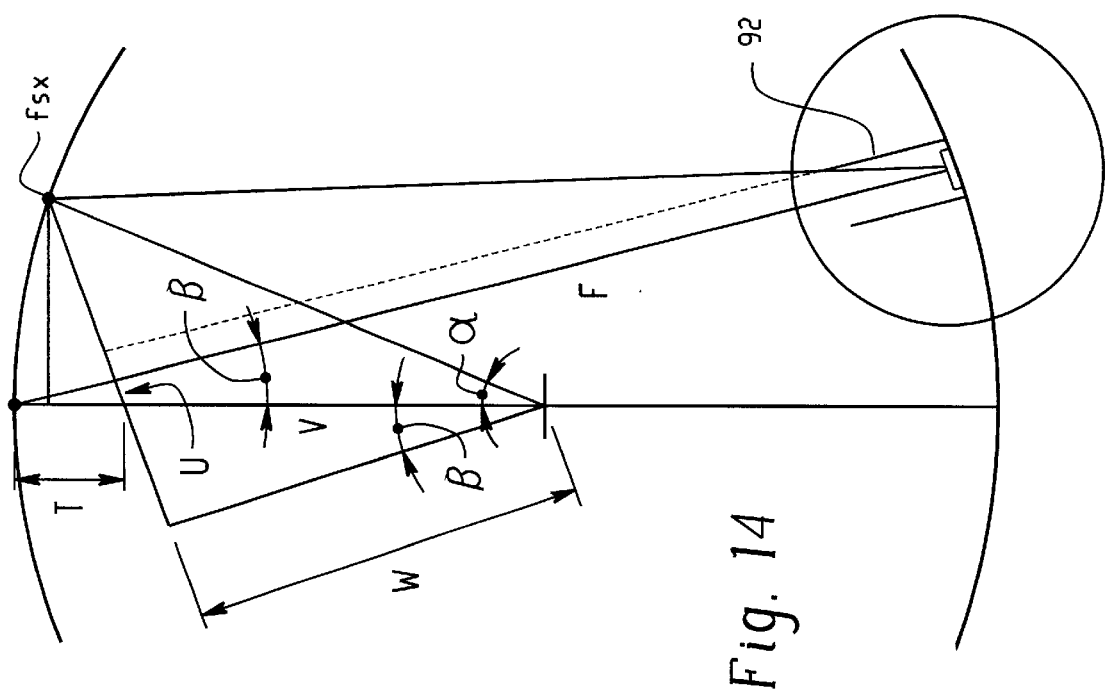
FIG. 14 illustrates the effect of scatter grids.
Figure 15A:
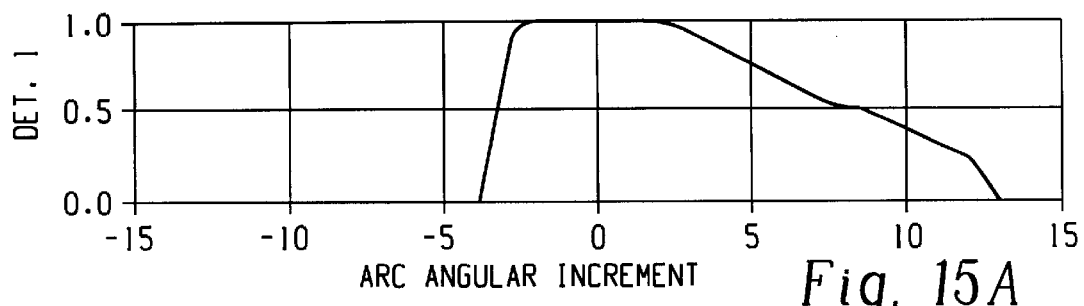
FIGS. 15A, 15B, 15C, 15D, and 15E illustrate off-focal shapes for various detectors in the detector arc; and, FIG. 16 illustrates a preferred deconvolution kernel.
Figure 15B:
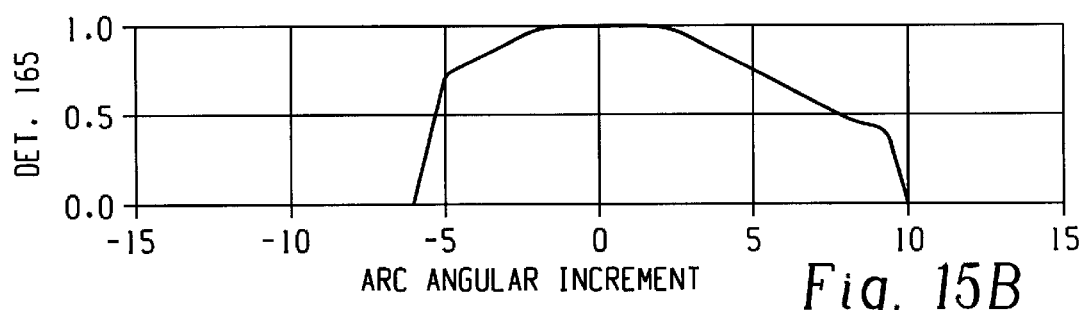
Figure 15C:
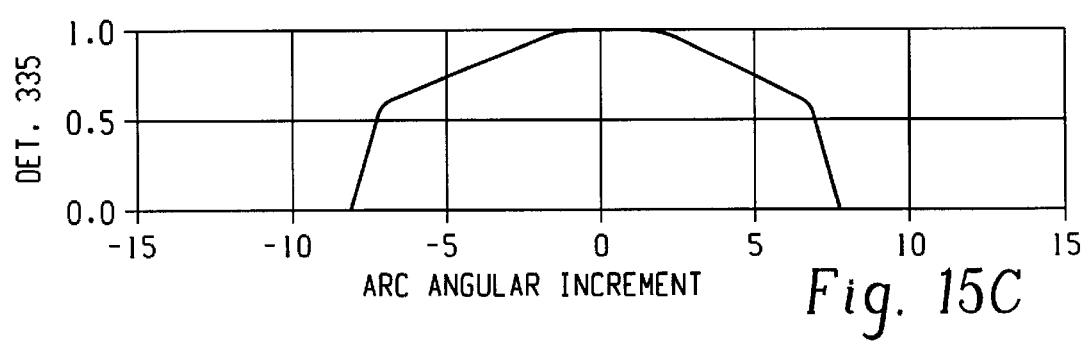
Figure 15D:
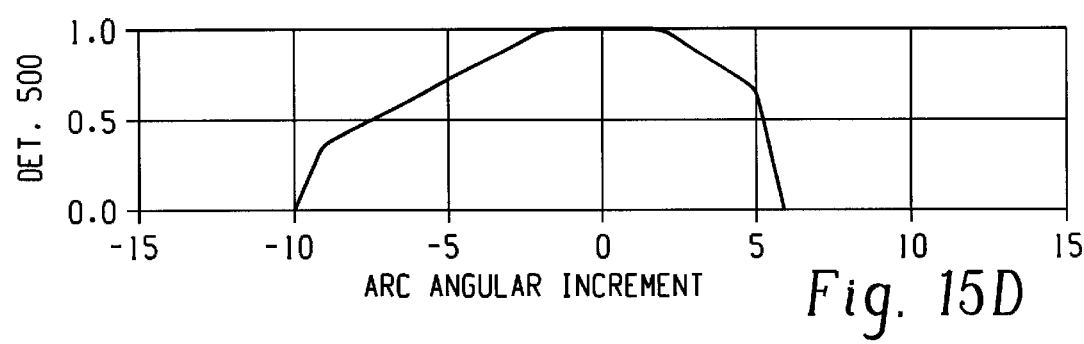
Figure 15E:
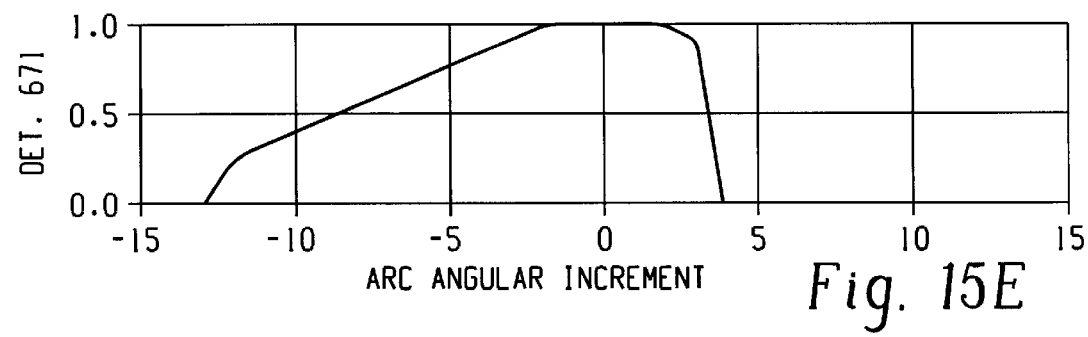

Referring to FIG. 14, the geometry of the scatter grids also determines the off-focal radiation that is visible to each detector. The scatter grids begin to cast a shadow on the detector blocking part of the detector from receiving off-focal radiation. As the off-focal angle increases, the shadow grows until the detector crystal is completely blocked by the anti-scatter grid. In order to find the shape of the off-focal radiation, the percentage of the crystal that is blocked by the anti-scatter grid at each angle a is determined. The position of the off-focal radiation spot is again defined as a fsx =S-sin a from which is defined:

$$W = S \cdot \cos(\alpha + \beta) \quad (15)$$
$$V = \frac{W}{\cos(\beta)}$$
$$T = S - V$$
$$U = \text{sign}(\alpha) \cdot T \cdot \sin(\beta)$$
$$F = \text{sign}(\alpha) \frac{fsx}{\sin(\beta)}$$

The two sides of the similar triangles are defined by:

$$P = F - U - \frac{d}{2} \quad \text{and} \quad (16)$$
$$a = (D + T \cdot \cos(\beta)) - h$$

The length of the shadow from the edge of the anti-scatter grid is:

$$shadow = \frac{p}{a} \cdot h \quad (17)$$

where h is the height of the edges of the anti-scatter grid. The percentage of the crystal covered by shadow is:

$$pct\_shadow = (shadow - ds/2)/cw \quad (18)$$

where ds is the dead space between the crystal and the scatter grid given by ds=d−cw. The percentage of x-rays reaching the crystal is equal to 1-pct_shadow. This x-ray percentage is defined as the shape of the off-focal radiation.

Combining the effects of the tube aperture and the anti-scatter grids generates maps of the off-focal radiation from the point of view of each detector as shown in FIGS. 15A–15E. The amplitude of the off-focal radiation is controlled by the scatter grid effects and the cut-off points at the edges are controlled by the tube aperture.

Figure 16:
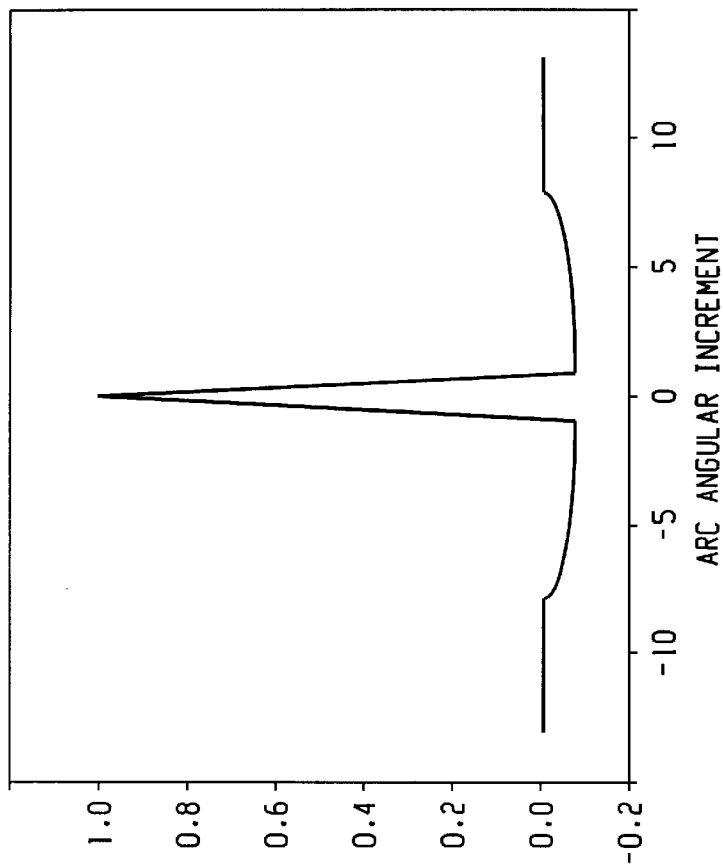

Because the cut-off for the radiation is an integer of source-fan increments (Equation 14), some of the kernels will vary in width from others. To simplify the correction, the total percentage of off-focal radiation that any detector sees is assumed to be a constant of_amp, which is a very close approximation. The off-focal kernel is normalized for each detector so that it sums to 1. To make the final deconvolution kernel, all of the off-focal radiation weightings are set negative and the center of the convolution function, which represents the on-focal component, is set equal to +1. A sample deconvolution kernel takes on the form shown in FIG. 10 and more accurately to scale in FIG. 16.

The off-focal radiation correction is made in the intensity domain, as opposed to the attenuation domain, where many other corrections are done. This is because the detectors measure an intensity related to the initial intensity of the x-rays and the attenuation along the beam path $I=I_0 \cdot e^{-\int\mu(l)dl}$. As in the off-focal radiation case, the initial intensity of the x-ray beam can vary. The expression for the intensity that each detector measures is $I=I_0 e^{-\int\mu(l)dl} + I_1 e^{-\int\mu(l_1)dl_1} + I_2 e^{-\int\mu(l_2)dl_2} + \ldots$. The logarithmic operation does not distribute over the off-focal expressions. Therefore, off-focal radiation is preferably removed in the intensity (unlogged) domain.

For each sample in the set of source fans, nearby detectors from nearby source fans are used to form an estimate of the off-focal radiation that was contributed to the sample and to perform a deconvolution. Two matrices are computed: one giving the detector indices to use for estimates for each detector and the other giving the shape of the off-focal kernel to use in the deconvolution. The weighting (off-focal shape) matrix $W_{k,m}$, where k is the source-fan angle and m is the sample index, and the matrix $N_{k,m}$ containing the detector indices are used for off-focal correction according to:

$$q(l, m) = p(l, m) + ofa \cdot \sum_{k} W_{k,m} \cdot p(l+k, m+k \cdot S_m) \quad (19)$$

where k∈{−ofw(1)ofw} is the index for the source angle increment of the off-focal radiation. This basic algorithm is used to identify nearby neighbors from nearby source fans to form an estimate of the off-focal radiation seen in each current sample. The summation process is performed according to Equation 19. In the preferred embodiment and as illustrated in FIG. 10, the correction is performed in four steps:

(1) for each new sample that is being corrected, work along one direction;
(2) multiple the value of each OF-estimate sample by the weight given in the kernel shape matrix;
(3) add the weighted value into the off-focal buffer; and
(4) repeat steps (1)–(3) until all OF-estimate samples have been included.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of generating diagnostic images comprising:
   rotating an x-ray source and a detector array concurrently around a subject in an examination region;
   measuring an intensity of x-rays which have traversed the subject with the array of radiation detectors, each detector generating an electronic data value which includes an on-focal radiation component and an off-focal radiation component, the array of detectors being sampled concurrently as the x-ray source and detector array rotate to generate a series of source-fan data lines;
   correcting the source fan data lines for off-focal radiation;
   reconstructing the off-focal radiation corrected data lines into an image representation.

2. The method as set forth in claim 1 wherein the off-focal radiation correcting step includes:
   correcting each data value of one data line by subtracting a fraction of data values of different source fan data lines sampled by different detectors.

3. The method as set forth in claim 1 further including:

converting the data values of each data line to attenuation values in a logarithmic domain;

performing preliminary corrections on the source fan data lines in the logarithmic domain; and storing the preliminary corrected source fan data sets in the logarithmic domain.

4. The method as set forth in claim 3 wherein the off-focal radiation correcting step includes:

converting data values from the logarithmic domain to a non-logarithmic domain and generating intensity values;

for each corrected intensity value, subtracting intensity values from other detectors from other source fan data lines in the non-logarithmic domain to generate an off-focal radiation corrected intensity value;

converting the off-focal radiation corrected intensity values into attenuation values in the logarithmic domain prior to the reconstructing step.

5. The method as set forth in claim 1 wherein the correcting step includes:

operating on a line of data values through a plurality of adjacent source fan data lines with a deconvolution function.

6. The method as set forth in claim 5 wherein the deconvolution function has a central value of unity aligned with an intensity value to be corrected and negative values to either side of the central value.

7. The method as set forth in claim 5 wherein the width of the deconvolution function is proportional to a width of an x-ray aperture in the x-ray source.

8. The method as set forth in claim 5 wherein an amplitude of negative portions of the deconvolution function vary in accordance with dimensions of a scatter-grid disposed adjacent the detector array.

9. The method as set forth in claim 5 wherein at least some neighboring intensity values are interpolated before the deconvolving step.

10. The method as set forth in claim 1 wherein the off-focal radiation step includes correcting for off-focal radiation both parallel to the axis of rotation and circumferentially around the axis of rotation.

11. The method as set forth in claim 6 further including:

selecting among a family of deconvolution functions in accordance with a location within the detector array of a detector corresponding to the intensity value being corrected.

12. An apparatus for generating diagnostic images comprising:

a rotating gantry mounted for rotation about a subject receiving bore;

an x-ray source mounted to the rotating gantry;

an array of x-ray detectors mounted to the rotating gantry across the subject receiving bore from the x-ray source, the detectors measuring an intensity of x-rays which have traversed the subject, each detector generating an electronic data value which includes an on-focal radiation component and an off-focal radiation component;

a means for sampling the array of detectors concurrently as the x-ray source and detector array rotate to generate a series of source-fan data lines;

a means for correcting the source fan data lines for off-focal radiation;

a means for reconstructing the off-focal radiation corrected data lines into an image representation.

13. The apparatus as set forth in claim 12 wherein the off-focal radiation correction means includes:

a means for correcting each data value of one data line by subtracting a fraction of data values of different source fan data lines sampled by different detectors.

14. The apparatus as set forth in claim 12 further including:

a means for converting the data values of each data line to attenuation values in a logarithmic domain;

a means for performing preliminary corrections on the source fan data lines in the logarithmic domain; and a means for storing the preliminary corrected source fan data lines in the logarithmic domain.

15. The apparatus as set forth in claim 14 wherein the off-focal radiation correction means includes:

a means for converting data values from the logarithmic domain to a non-logarithmic domain and generating intensity values;

a means for subtracting from each corrected intensity value intensity values from other detectors from other source fan data lines in the non-logarithmic domain to generate off-focal radiation corrected intensity values;

a means for converting the off-focal radiation corrected intensity values into attenuation values in the logarithmic domain.

16. The apparatus as set forth in claim 12 wherein the correction means includes:

a means for operating on a line of data values through a plurality of adjacent source fan data lines with a deconvolution function.

17. The apparatus as set forth in claim 16 wherein the deconvolution function has a central value of unity aligned with an intensity value to be corrected and negative values to either side of the central value.

18. The apparatus as set forth in claim 16 wherein the width of the deconvolution function is proportional to a width of an x-ray aperture in the x-ray source.

19. The apparatus as set forth in claim 16 further including:

a scatter grid disposed adjacent the detector array; and wherein an amplitude of negative portions of the deconvolution function vary in accordance with dimensions of the scatter-grid.

20. The apparatus as set forth in claim 16 further including:

a means for interpolating intensity values before deconvolving.

21. The apparatus as set forth in claim 5 further including:

a memory that stores a family of deconvolution function in accordance with a location within the detector array of a detector corresponding to the intensity value being corrected.

* * * * *